United States Patent
Park (10) Patent No.: US 11,574,727 B2
(45) Date of Patent: Feb. 7, 2023

(54) METHOD FOR FILTERING NORMAL MEDICAL IMAGE, METHOD FOR INTERPRETING MEDICAL IMAGE, AND COMPUTING DEVICE IMPLEMENTING THE METHODS

(71) Applicant: Lunit Inc., Seoul (KR)

(72) Inventor: Jongchan Park, Seoul (KR)

(73) Assignee: LUNIT INC., Seoul (KR)

( * ) Notice: Subject to any disclaimer, the term of this patent is extended or adjusted under 35 U.S.C. 154(b) by 175 days.

(21) Appl. No.: 17/077,142

(22) Filed: Oct. 22, 2020

(65) Prior Publication Data

US 2021/0391059 A1    Dec. 16, 2021

(30) Foreign Application Priority Data

Jun. 15, 2020 (KR) .................. 10-2020-0072257

(51) Int. Cl.
*G16H 30/40* (2018.01)
*G16H 50/20* (2018.01)
*G06T 7/00* (2017.01)

(52) U.S. Cl.
CPC .......... *G16H 30/40* (2018.01); *G06T 7/0012* (2013.01); *G16H 50/20* (2018.01); *G06T 2207/10116* (2013.01); *G06T 2207/20024* (2013.01); *G06T 2207/20081* (2013.01); *G06T 2207/30064* (2013.01)

(58) Field of Classification Search
None
See application file for complete search history.

(56) References Cited

U.S. PATENT DOCUMENTS

2019/0172576 A1* 6/2019 Knoplioch ............. G16H 40/67
2019/0189266 A1* 6/2019 Stoval, III ............. G16H 30/20
(Continued)

FOREIGN PATENT DOCUMENTS

| JP | 2012-088828 | 5/2012 |
| KR | 10-2012-0041468 | 5/2012 |
| KR | 10-2015-0077184 | 7/2015 |

(Continued)

OTHER PUBLICATIONS

Wang, C., Elazab, A., Jia, F. et al. Automated chest screening based on a hybrid model of transfer learning and convolutional sparse denoising autoencoder. BioMed Eng OnLine 17, 63 (2018). https://doi.org/10.1186/s 12938-018-0496-2 (Year: 2018).*

(Continued)

*Primary Examiner* — Samah A Beg
*Assistant Examiner* — Courtney Joan Nelson
(74) *Attorney, Agent, or Firm* — Lex IP Meister, PLLC (57) ABSTRACT

A method of reading a medical image by a computing device operated by at least one processor is provided. The method includes obtaining an abnormality score of the input image using an abnormality prediction model, filtering the input image so as not to be subsequently analyzed when the abnormality score is less than or equal to a cut-off score based on the cut-off score which makes a specific reading sensitivity; and obtaining an analysis result of the input image using a classification model that distinguishes the input image into classification classes when the abnormality score is greater than the cut-off score.

18 Claims, 10 Drawing Sheets

(56) References Cited

U.S. PATENT DOCUMENTS

2020/0151871 A1* 5/2020 Putha .................. G06F 40/30
2020/0160983 A1* 5/2020 Lyman ................ G06T 5/50

FOREIGN PATENT DOCUMENTS

| KR | 10-1639103 | 7/2016 | | |
|----|------------|--------|---|---|
| KR | 10-1880678 | 7/2018 | | |
| KR | 10-1943011 | 1/2019 | | |
| KR | 10-2019-0105460 | 9/2019 | | |
| KR | 10-2063492 | 1/2020 | | |
| WO | WO-2019245597 A1 * | 12/2019 | ............... | G06K 9/46 |

OTHER PUBLICATIONS

EPO, Search Report of EP 21178486.3 dated Nov. 9, 2021.

* cited by examiner

METHOD FOR FILTERING NORMAL MEDICAL IMAGE, METHOD FOR INTERPRETING MEDICAL IMAGE, AND COMPUTING DEVICE IMPLEMENTING THE METHODS

CROSS-REFERENCE TO RELATED APPLICATION

This application claims priority to and the benefit of Korean Patent Application No. 10-2020-0072257 filed in the Korean Intellectual Property Office on Jun. 15, 2020, the entire contents of which are incorporated herein by reference.

BACKGROUND

(a) Field

The present disclosure relates to an artificial intelligence-based medical image reading technology.

(b) Description of the Related Art

In the medical field, various products utilizing an artificial intelligence (AI) technology has been developing, and a diagnosis assistance system implemented with the AI-based medical image reading technology is a representative example thereof. The AI-based medical image reading technology can analyze the entire medical image with an AI algorithm and provide an abnormal lesion visually. A specialized doctor for image reading (hereinafter, referred to as a "reader") can be provided with an analysis result of the medical image from the diagnosis assistance system and read the medical image with reference thereto.

The reader can check a reading result provided by the diagnosis assistance system and medical records of a patient in a worklist, and can change the image reading order by way of worklist sorting based on specific criteria (e.g., emergency, abnormality, etc.). Using the function of worklist sorting, the reader can preferentially read an image required to be read urgently or an image where an abnormality is detected, rather than an image analyzed as normal. However, since the function worklist sorting is only to change the reading order of the images already included in the worklist, reading a normal image should be done at the end. Therefore, workload of the reader does not change.

In addition, although the reading level of the diagnosis assistance system has been increasing, reading sensitivity of the diagnosis assistance system is not very high due to the trade-off between the sensitivity and specificity.

SUMMARY

An embodiment is to provide a method of calculating an abnormality score of an input image using an abnormality prediction model, and filtering the input image whose abnormality score is less than or equal to a cut-off score into strong normal, based on the cut-off score which determines a specific sensitivity.

Another embodiment is to provide a method of creating a worklist for performing subsequent classification analysis on images that are not strong normal and excluding images classified into strong normal from the worklist, through a two-stage analysis including strong normal filtering.

Yet another embodiment is to provide a method of cutting off multiple diseases whose disease prediction difficulties are different with the same sensitivity, and a calibration method for performing the same.

According to an embodiment, a method of reading a medical image by a computing device operated by at least one processor is provided. The method includes obtaining an abnormality score of the input image using an abnormality prediction model, filtering the input image so as not to be subsequently analyzed when the abnormality score is less than or equal to a cut-off score based on the cut-off score which makes a specific reading sensitivity, and obtaining an analysis result of the input image using a classification model that distinguishes the input image into classification classes when the abnormality score is greater than the cut-off score.

The input image whose abnormality score is less than or equal to the cut-off score may be classified into strong normal.

The classification model may include an artificial intelligence model that has learned a task of distinguishing the input image into weak normal or abnormal.

The method may further include adding the analysis result to a reading worklist, and the input image whose abnormality score is less than or equal to the cut-off score may be not added to the reading worklist.

In a case of the input image whose abnormality score is less than or equal to the cutoff score, a filtering result may be added to a separate report from the reading worklist.

Obtaining the abnormality score may include, when obtaining disease prediction scores for different diseases from the abnormality prediction model, aggregating the disease prediction scores to determine the abnormality score.

Obtaining the abnormality score may include, obtaining calibrated disease prediction scores based on calibration that converts a cut-off score for each disease, which makes the specific reading sensitivity, into the cut-off score, and determining a maximum value among the calibrated disease prediction scores as the abnormality score.

In a case where each of disease prediction scores for different diseases is obtained as an abnormality score for each disease from the abnormality prediction model, filtering the input image may include calculating a cut-off score for each disease which makes the specific reading sensitivity, and filtering the input image when the abnormality score for each disease is less than or equal to the cut-off score for a corresponding disease, for all of the different diseases.

The abnormality prediction model may include a feature extraction model trained to output a feature of the input image, and at least one disease prediction head model trained to predict at least one disease based on features output from the feature extraction model.

The abnormality prediction model may have a sensitivity between 90% and 100%.

According to another embodiment, a method of reading a medical image by a computing device operated by at least one processor is provided. The method includes setting a cut-off score that makes a specific reading sensitivity for an abnormality prediction model that outputs an abnormality score of a medical image; obtaining an abnormality score of an input image using the abnormality prediction model; and when the abnormality score of the input image is less than or equal to the cut-off score, classifying the input image into strong normal and filtering the input image so as not to be subsequently analyzed.

The method may further include obtaining an analysis result of the input image using a classification model that distinguishes between weak normal and abnormal when the abnormality score of the input image is greater than the cut-off score.

The method may further include adding the analysis result to a reading worklist, and the input image classified into strong normal may be not added to the reading worklist.

Obtaining the abnormality score may include, when obtaining disease prediction scores for different diseases from the abnormality prediction model, calibrating the disease prediction scores so as to provide the specific reading sensitivity for the different diseases at the cut-off score, and determining a maximum value among the calibrated disease prediction scores as the abnormality score of the input image.

In a case where each of disease prediction scores for different diseases from the abnormality prediction model is obtained as an abnormality score for each disease, filtering the input image may include calculating a cut-off score for each disease which makes the specific reading sensitivity, and filtering the input image when the abnormality score for each disease is less than or equal to the cut-off score for a corresponding disease, for all of the different diseases.

According to yet another embodiment, a method of reading a medical image by a computing device operated by at least one processor is provided. The method includes inputting an input image to an abnormality prediction model that outputs an abnormality score of a medical image, obtaining disease prediction scores for a plurality of diseases from the abnormality prediction model, calibrating the disease prediction scores so as to provide a same reading sensitivity for the plurality of diseases at a same cut-off score, determining a maximum value among the calibrated disease prediction scores as an abnormality score of the input image, and when the abnormality score of the input image is less than or equal to the cut-off score, classifying the input image into strong normal and filtering the input image so as not to be subsequently analyzed. The abnormality prediction model may include a feature extraction model trained to output a feature of the input image, and a plurality of disease prediction head models that are trained to predict the plurality of diseases based on features output from the feature extraction model.

The input image may include a chest x-ray image, and the plurality of diseases may include at least two of consolidation, nodule, and pneumothorax.

The reading sensitivity may have a value between 90 and 100%.

The method may further include obtaining an analysis result of the input image using a classification model that distinguishes between weak normal and abnormal when the abnormality score of the input image is greater than the cut-off score, and adding the analysis result to a reading worklist. The input image classified into strong normal may be not added to the reading worklist.

According to still another embodiment, a computing device including a memory and a processor is provided. The memory stores an abnormality prediction model trained to output an abnormality score of an input image, and a classification model trained to distinguish the input image into weak normal and abnormal. The processor obtains an abnormality score of the input image using the abnormality prediction model, classifies the input image into strong normal and filters the input image so as not to be subsequently analyzed when the abnormality score of the input image is less than or equal to a cut-off score, and obtains an analysis result of the input image using the classification model that distinguishes the input image into classification classes when the abnormality score of the input image is greater than the cut-off score.

The abnormality prediction model may include a feature extraction model trained to output a feature of the input image, and at least one disease prediction head model trained to predict at least one disease based on features output from the feature extraction model.

In general image medical diagnosis, most cases are normal cases where there is nothing abnormal. According to some embodiments, since strong normal images corresponding to definite normal cases are excluded from a worklist, a workload of a reader can be significantly reduced.

According to some embodiments, a computing device does not perform a subsequent analysis on images classified into strong normal and intensively analyzes only images other than the strong normal images, thereby improving computing efficiency.

According to some embodiment, since the input image is analyzed using an artificial intelligence model that has learned a difficult task of distinguishing between weak normal and abnormal, it is possible to improve the performance of distinguishing between weak normal and abnormal.

According to some embodiments, it is possible to filter strong normal images with a high sensitivity, and particularly, even if the distribution of abnormality scores of multiple diseases is different according to a difference in abnormality prediction difficulties, strong normal images can be filtered with a single cut-off score.

DETAILED DESCRIPTION

In the following detailed description, exemplary embodiments of the present disclosure will be described in detail with reference to the accompanying drawings so that those of ordinary skill in the art may easily implement the present disclosure. However, the present disclosure may be implemented in various different forms and is not limited to the embodiments described herein. Accordingly, the drawings and description are to be regarded as illustrative in nature and not restrictive. Like reference numerals designate like elements throughout the specification.

As used herein, unless explicitly described to the contrary, the word "comprise", "include" or "have", and variations such as "comprises", "comprising", "includes", "including", "has" or "having" will be understood to imply the inclusion of stated elements but not the exclusion of any other elements. In addition, the term "unit", "-er", "-or" or "module" described in the specification mean a unit for processing at least one function and operation, and may be implemented by hardware components or software components, and combinations thereof.

As used herein, a task refers to an assignment to be solved through machine learning or work to be done through machine learning. For example, in a case of performing recognition, classification, and prediction from a medical image, each of the recognition, classification, and prediction may correspond to an individual task. An artificial intelligence model of the present disclosure is a model for learning at least one task, and may be implemented as software or a program to be executed on a computing device. The program is stored in a storage medium (non-transitory storage media) and includes instructions for executing operations of the present disclosure by a processor. The program may be downloaded via a network, or sold as a product.

The present disclosure may be applied to medical images of various areas photographed with various modalities. For example, the modalities of medical images may be X-ray, magnetic resonance imaging (MRI), ultrasound, computed tomography (CT), mammography (MMG), or digital breast tomosynthesis (DBT). In the specification, a chest X-ray image may be described as an example.

A general diagnosis assistance system analyzes an input image as normal or abnormal based on a cut-off score. The cut-off score is determined by adjusting the trade-off between sensitivity and specificity. If the sensitivity is set very high, false positives increase and the specificity decreases, resulting in increased user fatigue. Therefore, the existing diagnosis assistance systems set the reading sensitivity not very high so that the images analyzed as normal require a doctor's reading. However, since most cases are normal cases having no abnormality, it is required to improve the efficiency of the reading work.

In order to solve this issue, the present disclosure filters the images determined that is definitely normal so as not to require the doctor's reading. Such non-suspicious and definite normal is referred to as "strong normal". Among the normal cases, a case that is not strong normal and thus requires the doctor's reading is referred to as a "weak normal".

Figure 1:
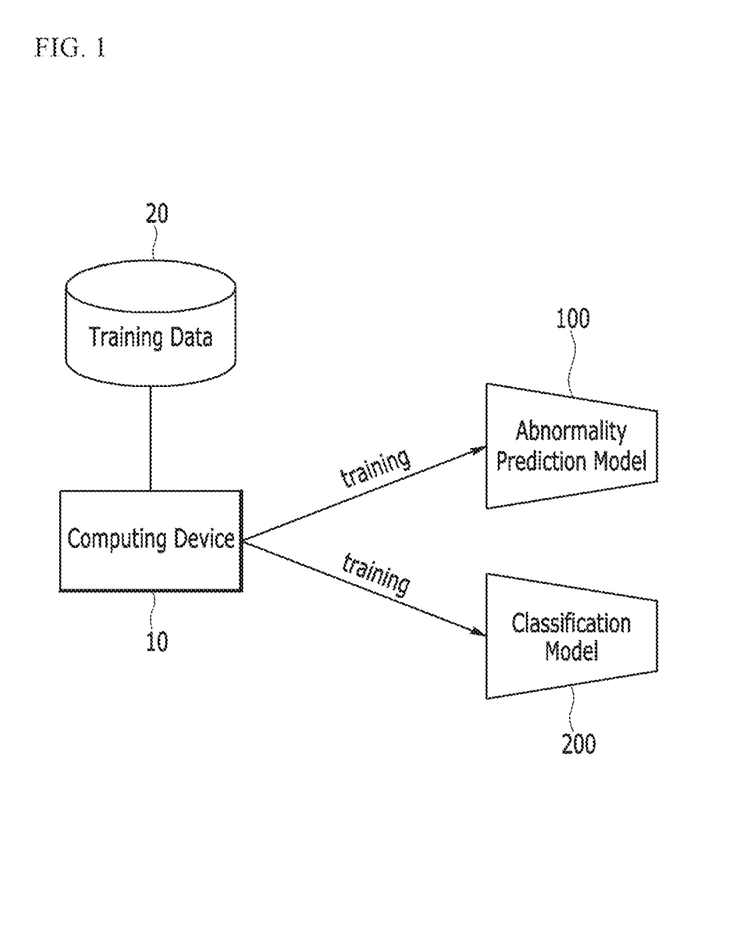
FIG. 1 is a drawing illustrating learning of an abnormality prediction model and a classification model according to an embodiment.
Figure 2:
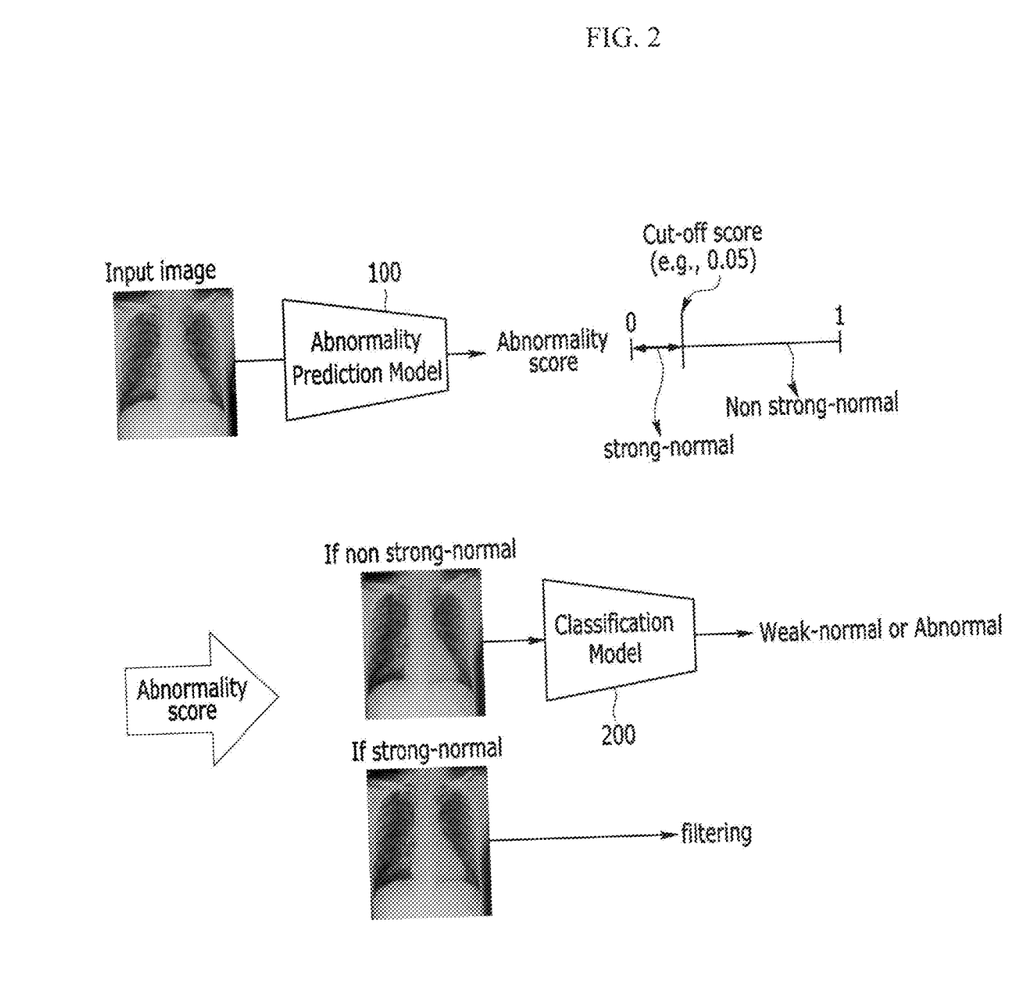
FIG. 2 is a drawing schematically showing a two-stage analysis including strong normal filtering according to an embodiment.

FIG. 1 is a diagram for explaining learning of an abnormality prediction model and a classification model according to an embodiment, and FIG. 2 is a diagram schematically showing a two-stage analysis including strong normal filtering according to an embodiment.

Referring to FIG. 1, a computing device 10 operated by at least one processor may train an abnormality prediction model 100, which is an artificial intelligence model, using at least some of training data 20. The abnormality prediction model 100 may learn about a task of predicting an abnormality for features of a medical image and outputting the predicted result as an abnormality score. Here, the abnormality prediction model 100 is used to filter out a definite normal image (hereinafter referred to as a "strong normal" image) among input images, and has a high reading sensitivity. For example, the abnormality prediction model 100 may have a very high sensitivity between 90% and 100%. Hereinafter, it is described that the abnormality prediction model 100 has an ultrahigh sensitivity of 99%.

The computing device 10 may train the abnormality prediction model 100 by assigning a weight to abnormal images among the training data 20. The computing device 10 may train the abnormality prediction model 100 by assigning the weight to the abnormal images that are difficult to be classified, and iteratively train the abnormality prediction model 100 on the abnormal images that are difficult to be classified. The computing device 10 may train the abnormality prediction model 100 by adjusting the abnormal images to maintain a specific ratio in an objective function.

The computing device 10 may train a classification model 200, which is an artificial intelligence model, using at least some of the training data 20. The classification model 200 may learn a classification task using the training data annotated with weak normal and abnormal other than strong normal. That is, the classification model 200 may intensively learn a difficult task of distinguishing the input image into weak normal or abnormal. The classification model 200 may be implemented with various neural networks that can classify input features into classification classes. Here, "weak normal" means a case that can be suspicious as malignant but is normal, and is used to distinguish normal into strong normal and normal that is not strong normal.

Referring to FIG. 2, a computing device 10 performs a two-stage analysis including strong normal filtering using the learned abnormality prediction model 100 and the learned classification model 200.

First, the computing device 10 may calculate an abnormality score of an input image using the learned abnormality prediction model 100, and may classify and filter the input image whose abnormality score is less than or equal to a cut-off score (e.g., 0.05) into strong normal, based on the cut-off score which makes (or sets) a specific reading sensitivity (e.g., 99%). In this way, the computing device 10 may classify input images into strong normal images and the remaining images, and filter out the strong normal images so that no subsequent classification analysis is performed on the strong normal images. Then, the computing device 10 may perform the subsequent analysis for classifying or differentiating the remaining images into classes other than the strong normal class. The classes other than strong normal class may include, for example, weak normal and abnormal, and may be further subdivided.

The computing device 10 classifies the remaining unfiltered images into the classes such as weak normal or abnormal, using the learned classification model 200. The images with the classification result other than strong normal, such as weak normal or abnormal, are added to a reading worklist (hereinafter, referred to as a "worklist"). Thereafter, when a reader selects an input image from the worklist, the analysis result (disease position or disease prediction score, etc.) obtained by using the classification model 200 may be visually displayed on the input image. The visual display method may be selected from among various methods including secondary capture.

The computing device 10 filters and classifies the input images according to the abnormality score, as in Table 1. The image classified into strong normal is not further analyzed and is excluded from the worklist. The image that is not filtered out and is analyzed as normal (weak normal) is not excluded from the worklist and is required to be checked by the reader. For the image analyzed as abnormal, a heatmap visually indicating a position or predicted value of an abnormal lesion may be displayed.

TABLE 1

| Abnormality Score | Case | Action |
| --- | --- | --- |
| [0, 0.05) | Strong normal | Excluded from worklist |
| [0.05, 0.15) | Normal/weak normal | Not excluded from worklist, and Required to be checked by reader |
| [0.15, 1.0] | Abnormal | Abnormal heatmap shown |

In this way, the computing device 10 may exclude the strong normal images from the worklist by filtering them through the two-stage analysis including strong normal filtering based on the abnormality score and the subsequent analysis, and add only the remaining images including the results of the subsequent analysis to the worklist. Since the images filtered as strong normal have a very low probability of abnormal lesions, there is no need to perform the subsequent analysis for them and to add them to the worklist that is required to be read by the reader unlike the images that are not strong normal. On the other hand, the analysis result of the images filtered as strong normal may be prepared as a report in a different form than the worklist.

The worklist is a list of images that are required to be read by a reader in a reading procedure, and, in a broad sense, may mean a list of various tasks including medical actions related to patients in a medical institution. Because the worklist merely includes images classified into non-strong normal cases (e.g., weak normal and abnormal cases), unnecessary reading work for strong normal cases that are clearly normal may be reduced. Since a ratio of the strong normal cases varies depending on an image modality and a type of disease, the reduction ratio of the reading workload may be different. In the normal cases that occupy the majority, the workload of the reader can be significantly reduced because the strong normal images are excluded from the worklist. When a specific verification set is checked after a cut-off score of 0.05, in which the sensitivity for the abnormal prediction model 100 becomes 99%, is set, more than half of the normal images are filtered as strong normal so that more than half of the normal images may be excluded from the worklist.

Although a task of training the abnormal prediction model 100, a task of filtering strong normal cases using the abnormality prediction model 100, a task of training the classification model 200, and a classifying or distinguishing task using the classification model 200 may be implemented over a plurality of computing devices in a distributed manner, it is assumed that the computing device 10 performs operations of the present disclosure for convenience of description. For example, after a specific computing device trains the abnormality prediction model 100 and/or the classification model 200, and the learned abnormality prediction model 100 and the classification model 200 may be installed to computing devices positioned at a hospital, the image reading based on the two-stage analysis may be performed. Alternatively, after the learned abnormality prediction model 100 and classification model 200 may be installed to a server device, the computing devices positioned in the hospital may transmit an image to the server device, receive the analysis result of the image from the server device, and then add the analysis result to the worklist.

Figure 3A:
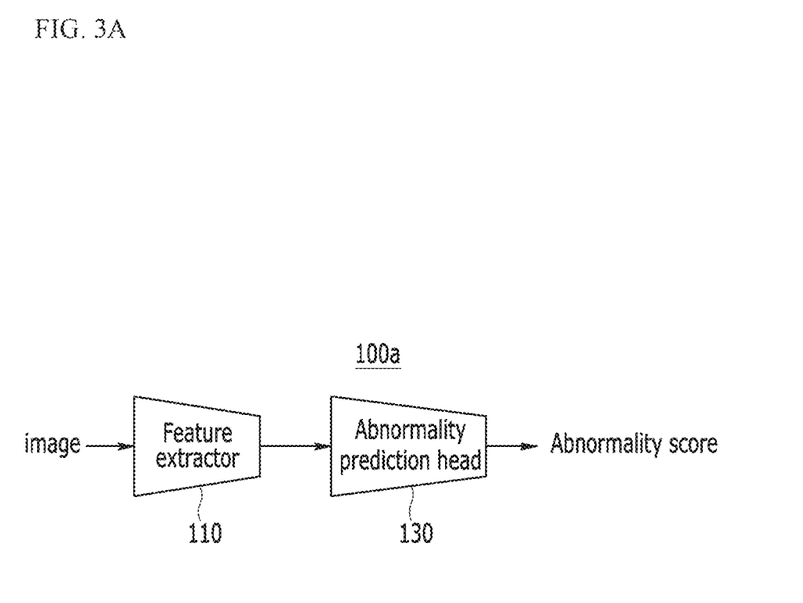
FIG. 3A and FIG. 3B show an example of an abnormality prediction model according to an embodiment.
Figure 3B:
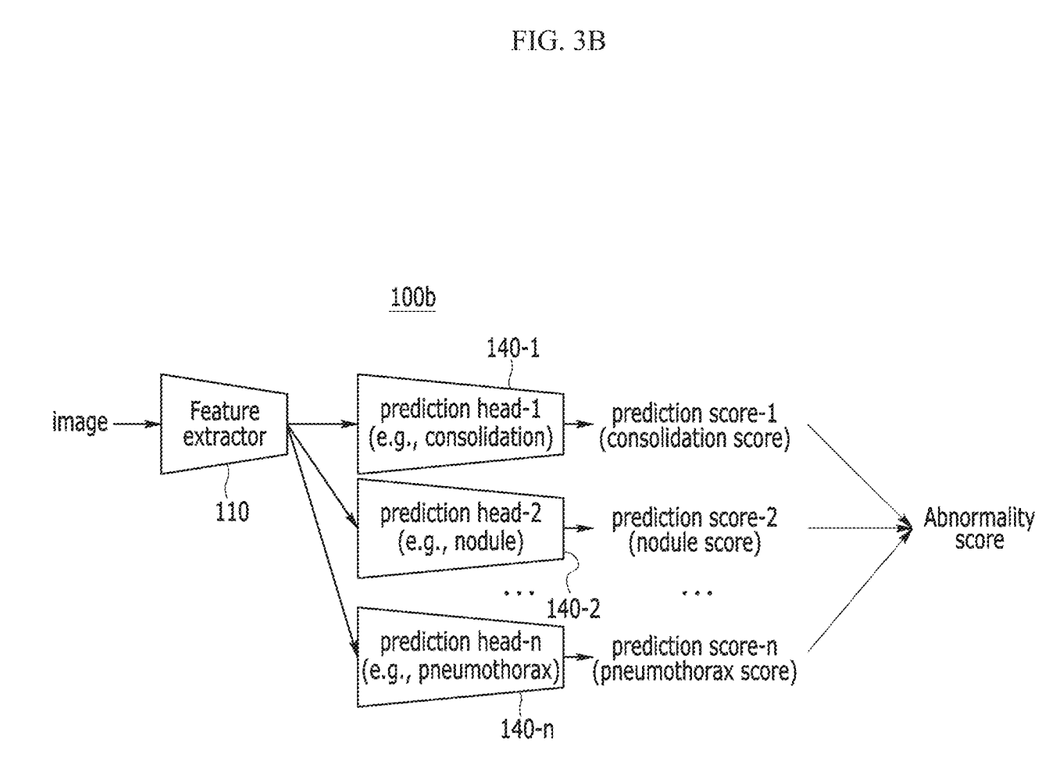

FIG. 3A and FIG. 3B show an example of an abnormality prediction model according to an embodiment.

Referring to FIG. 3A and FIG. 3B, an abnormality prediction model 100a or 100b may be designed as a single-headed network or a multi-headed network. For example, the abnormality prediction model 100a or 100b may include a feature extractor for extracting a feature of an input image, and one abnormality/disease prediction head model.

Referring to FIG. 3A, the abnormality prediction model 100a designed as the single-head network may include a feature extraction model 110 and an abnormality prediction head model 130. The feature extraction model 110 is a neural network model trained to extract a feature for detecting a lesion from an input image, and outputs the feature of the input image. The abnormality prediction head model 130 is a neural network model trained to predict an abnormality probability for the features output from the feature extraction model 110, and outputs a prediction result as an abnormality score.

When obtaining the abnormality score of the input image using the learned abnormality prediction model 100a, a computing device 10 may classify and filter the input image whose abnormality score is less than or equal to a cut-off score into strong normal, based on the cut-off score for making a desired reading sensitivity (e.g., 99%).

Referring to FIG. 3B, the abnormality prediction model 100b designed as the multi-head network may include a feature extraction model 110 and a plurality of disease prediction head models 140-1, 140-2, . . . , 140-n. Each disease prediction head model is a neural network model trained to predict a corresponding disease, and outputs the prediction result as a corresponding disease prediction score. Although the disease prediction score may correspond to the abnormality score, a score output from the disease prediction head model may be called the disease prediction score in order to distinguish it from the abnormality score calculated by combining the disease prediction scores.

The plurality of disease prediction head models 140-1 to 140-n) may be configured in parallel according to types of diseases (lesions or findings) that can be analyzed in an image photographed with a specific modality. For example, when the input image is a chest X-ray image, the abnormality prediction model 100 may include the disease prediction head models that independently predict consolidation, nodule, and pneumothorax, respectively.

In a case of the abnormality prediction model 100b, each of the plurality of disease prediction head models 140-1 to 140-n) is independently trained based on learning data related to a corresponding disease. In this case, a prediction difficulty of each disease may be different, and an amount of training data related to each disease may be different. Therefore, since the distribution of disease prediction scores output from each disease prediction head model is different, the disease prediction score that becomes the desired reading sensitivity (e.g., 99%) may be different for each disease. If the strong normal images and the remaining images are classified based on the same cut-off score (e.g., 0.05), the reading sensitivity may vary for each disease. For example, a lesion that is easy to detect may be sensitively detected, and a lesion that is difficult to detect may be detected less sensitively. In order to solve this issue, a method of filtering images so as to allow the computing device 10 to provide the same reading sensitivity (e.g., 99%) regardless of a disease type is described below.

Figure 4:
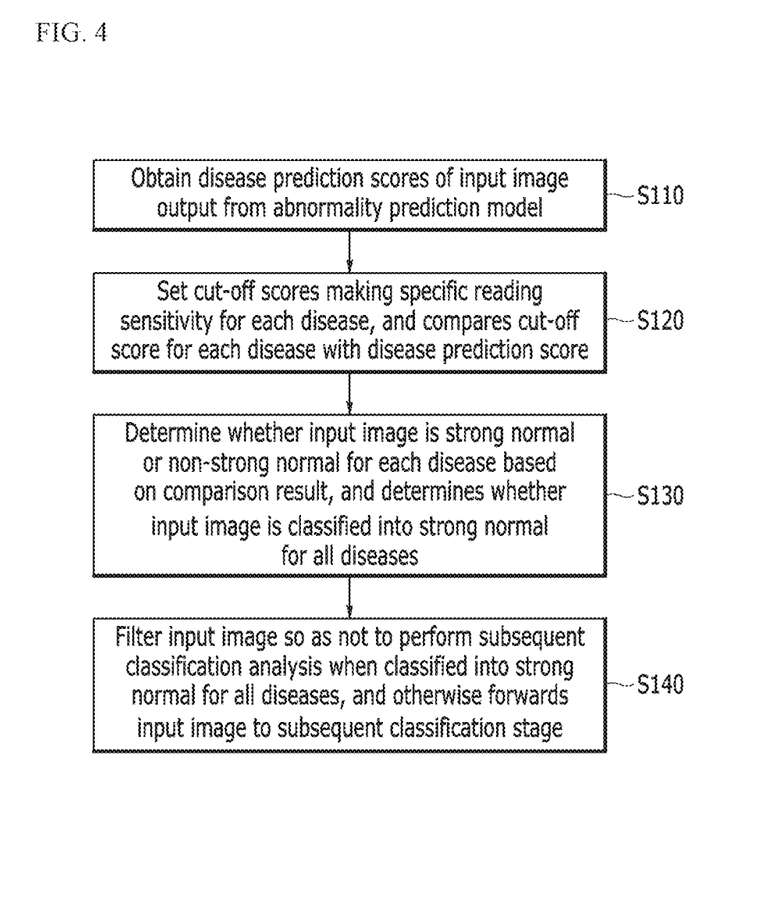
FIG. 4 and FIG. 5 each are a flowchart of a strong normal filtering method according to an embodiment.
Figure 5:
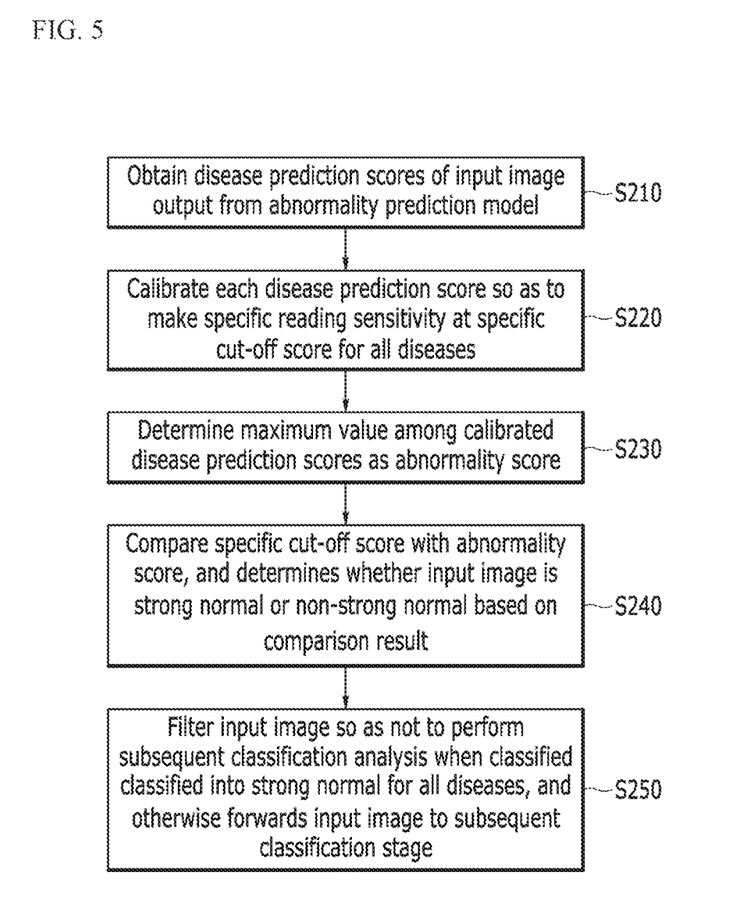

FIG. 4 and FIG. 5 each are a flowchart of a strong normal filtering method according to an embodiment.

Referring to FIG. 4, a computing device 10 obtains disease prediction scores (e.g., a consolidation score, a nodule score, and a pneumothorax score) of an input image that are output from disease prediction head models of an abnormality prediction model 100b, respectively (S110).

The computing device 10 sets cut-off scores C1, C2, and C3 which make a specific reading sensitivity (e.g., 99%) for each disease, and compares the cut-off score for each disease with the disease prediction score (S120). Here, the cut-off score for each disease may not be the same. If the disease prediction score is less than the cut-off score, the input image is filtered as strong normal.

The computing device 10 determines whether the input image is strong normal or non-strong normal for each disease based on the comparison result, and determines whether the input image is classified into strong normal for all of the plurality of diseases (S130). The input image with the disease prediction score less than or equal to the cut-off score is classified into strong normal, and the input image with the disease prediction score greater than the cut-off score is classified into non-strong normal.

The computing device 10 filters the input image so as not to perform a subsequent classification analysis when the input image is classified into strong normal for all of the plurality of diseases, and forwards the input image to a subsequent classification stage when the input image is not classified into strong normal for all of the plurality of diseases (S140).

That is, the computing device 10 finally classifies the input image as strong normal when the input image is classified into strong normal for all of the plurality of diseases, and determines that the input image is not strong normal when the input image is not classified into strong normal for all of the plurality of diseases. For example, when all of the consolidation score, nodule score and pneumothorax score predicted for the input image are less than or equal to the cut-off score of the corresponding disease, the input image is classified into strong normal. The input image classified into strong normal is not added to a worklist, unlike an image on which the subsequent classification analysis is to be performed. Instead, the computing device 10 may create a separate report, which is distinguished from the worklist, for the input image classified into strong normal.

Referring to FIG. 5, a computing device 10 obtains disease prediction scores (e.g., a consolidation score, a nodule score, and a pneumothorax score) of an input image that are output from disease prediction head models of an abnormality prediction model 100b, respectively (S210).

The computing device 10 calibrates each disease prediction score so as to make a specific reading sensitivity (e.g., 99%) at a specific cut-off score (e.g., 0.05) for all diseases (S220).

The computing device 10 determines a maximum value among the calibrated disease prediction scores as an abnormality score (S230).

The computing device 10 compares a specific cut-off score of 0.05 with the abnormality score, and determines whether the input image is strong normal or non-strong normal based on the comparison result (S240).

The computing device 10 filters the input image so as not to perform a subsequent classification analysis when the input image is classified into strong normal, and forwards the input image to a subsequent classification stage when the input image is not classified into strong normal (S250). The computing device 10 may create a separate report for the input image classified into strong normal without adding the analysis result to the worklist.

The computing device 10 may calibrate each disease prediction score as follows. The calibrated disease prediction scores may be calculated based on calibration that converts the cut-off score for each disease, which makes the specific reading sensitivity, into the same cut-off score. As a result, even if the input image is classified into strong normal at a single cut-off score, the same reading sensitivity for all diseases may be provided.

For example, assuming that a cut-off score for making a sensitivity of 99% in a pneumothorax prediction head model is c1, a pneumothorax score y1 may be converted into a pneumothorax score y1' through Equation 1, in order to shift the cut-off score c1 to a specific score (e.g., 0.05).

$$y1' = \frac{y*0.5}{c1}, \text{if } y1 \leq c1$$
$$y1' = \frac{(y1-c1)*(1-0.05)}{1-c1} + 0.05, \text{if } y1 > c1$$

Equation 1

Similarly, assuming that a cut-off score for making a sensitivity of 99% in a consolidation prediction head model is c2, a consolidation score y2 may be converted into a calibrated consolidation score y2' as in Equation 1.

Assuming that a cut-off score for making a sensitivity of 99% in a nodule prediction head model is c3, a nodule score y3 may be converted into a calibrated nodule score y3' as in Equation 1.

The computing device 10 determines a maximum value among the calibrated disease prediction scores y1', y2', and y3' as an abnormality score, and compares the cut-off score of 0.05 with the abnormality score. If the abnormality score is less than or equal to the cut-off score of 0.05, the input image is classified into strong normal.

Figure 6A:
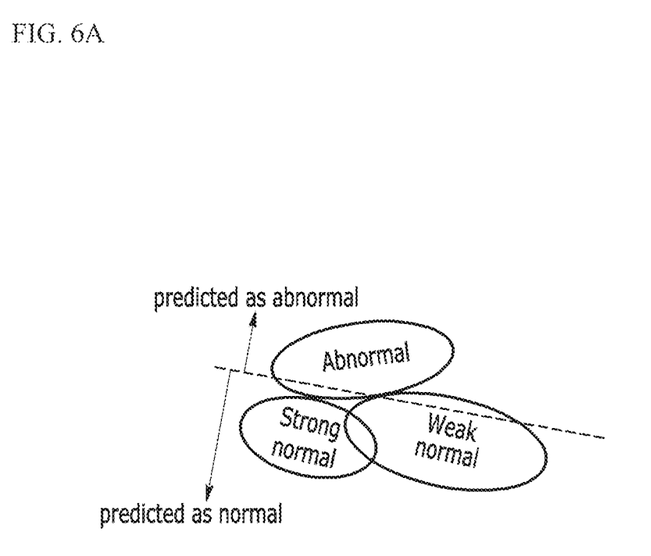
FIG. 6A and FIG. 6B are drawings schematically illustrating a merit of a two-stage analysis including strong normal filtering according to an embodiment.
Figure 6B:
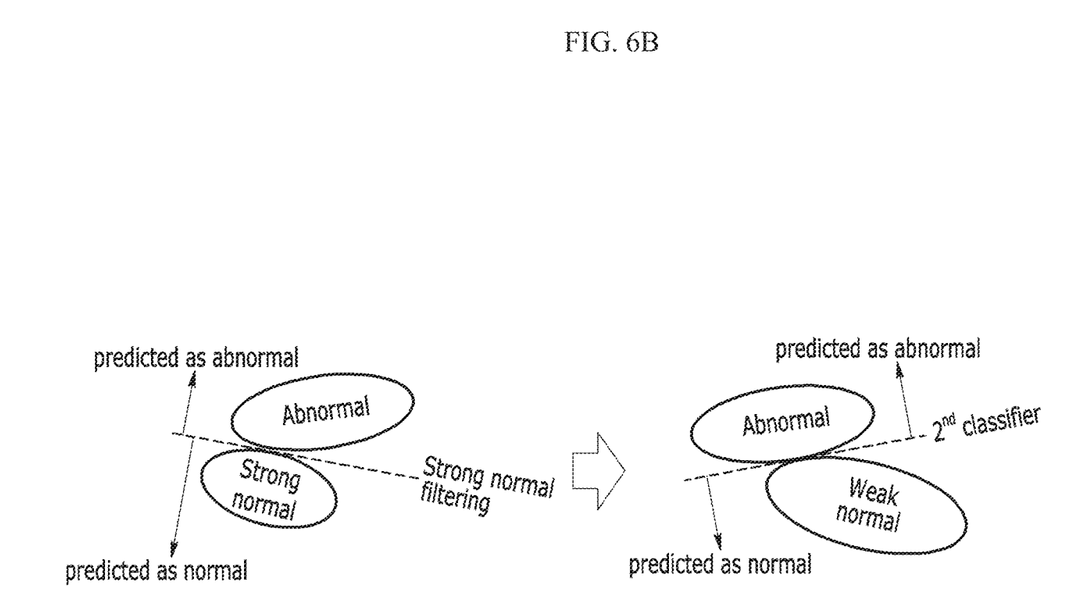

FIG. 6A and FIG. 6B are drawings schematically illustrating a merit of a two-stage analysis including strong normal filtering according to an embodiment.

Referring to FIG. 6A, a general classification model is trained to distinguish normal including strong normal and weak normal from abnormal. Since distinguishing input features into weak normal and abnormal is difficult compared to distinguishing the input features into strong normal and abnormal, the general classification model tends to perform learning more easily and does not properly learn a task for distinguishing between weak normal and abnormal.

On the other hand, as shown in FIG. 6B, a computing device 10 can filter images predicted as strong normal through strong normal filtering to exclude them from subsequent classification, and classify input features into weak normal and abnormal through a classification model 200 for distinguishing between weak normal and abnormal. The classification model 200 may intensively learn a difficult task for distinguishing between weak normal and abnormal, and thus can have high classification performance.

The computing device 10 may add the analysis result on the input image of the classification model 200 to the worklist. The analysis result may include a detection result for at least one disease (e.g., consolidation, nodule, pneumothorax, etc.) that can be analyzed in modality.

Figure 7:
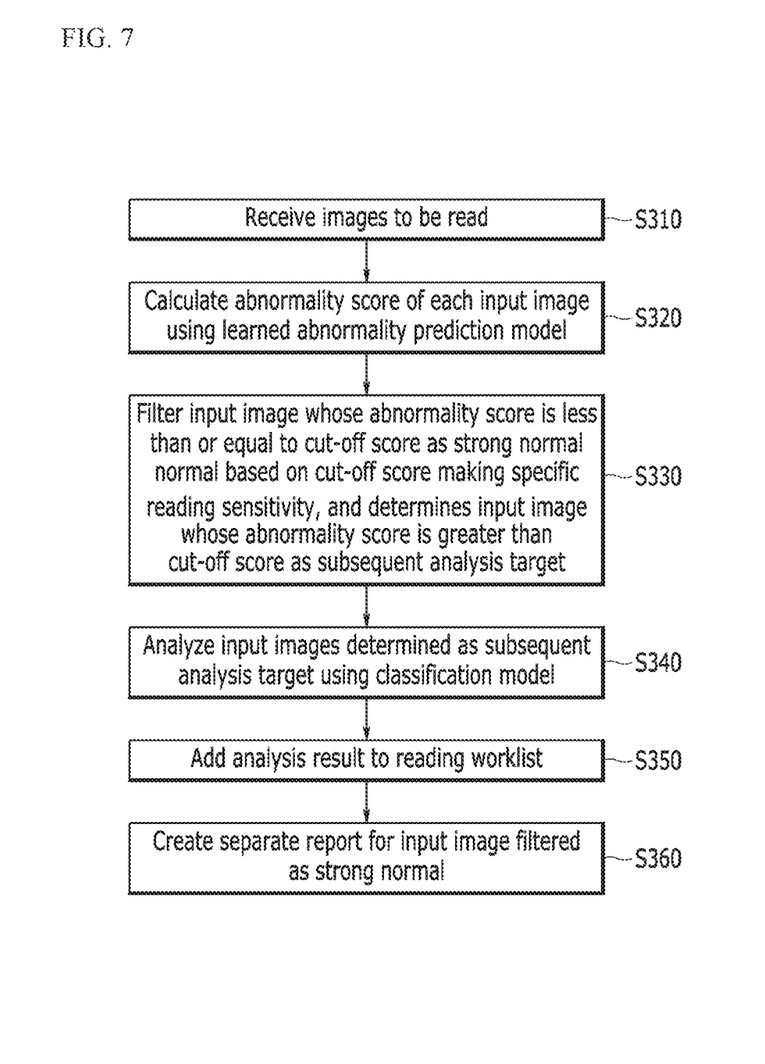
FIG. 7 is a flowchart of a medical image reading method according to an embodiment.

FIG. 7 is a flowchart of a medical image reading method according to an embodiment.

Referring to FIG. 7, a computing device 10 receives images to be read (S310).

The computing device 10 calculates an abnormality score of each input image using the learned abnormality prediction model 100 (S320). The abnormality prediction model 100 may be an abnormality prediction model 100a configured with a single-head network or an abnormality prediction model 100b configured with a multi-head network. The computing device 10 may calibrate a plurality of disease prediction scores output from abnormality prediction models 100b so as to make the same reading sensitivity at the same cut-off score for all diseases. Further, the computing device 10 may determine a maximum value among the calibrated disease prediction scores as the abnormality score.

The computing device 10 filters an input image whose abnormality score is less than or equal to the cut-off score as strong normal, based on a cut-off score that makes a specific reading sensitivity, and determines an input image whose abnormality score is greater than the cut-off score as a subsequent analysis target (S330).

The computing device 10 performs an analysis of distinguishing the input images determined as the subsequent analysis target into classification classes (e.g., weak normal and abnormal) using a classification model 200 (S340).

The computing device 10 adds the analysis result to a worklist that is required to be read by a reader (S350).

The computing device 10 may create a separate report for the input image filtered as strong normal (S360).

Figure 8:
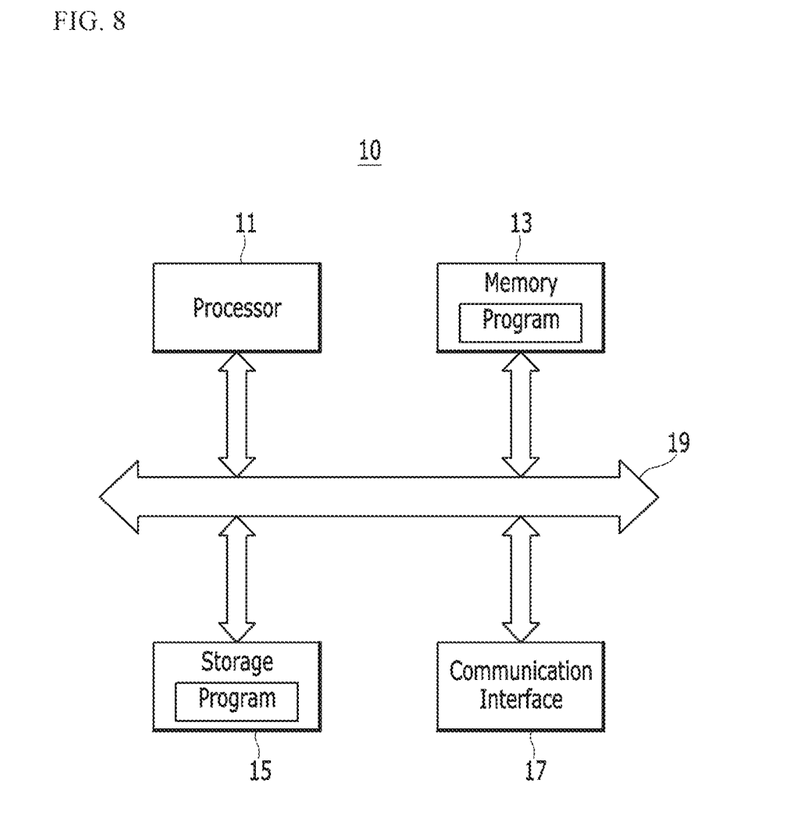
FIG. 8 is a configuration diagram of a computing device according to an embodiment.

FIG. 8 is a configuration diagram of a computing device according to an embodiment.

Referring to FIG. 8, a computing device 10 may include one or more processors 11, a memory 13 on which a computer program to be executed by the processor 11 is loaded, a storage 15 which stores the program and various data, a communication interface 17, and a bus 19 for connecting them. In addition, the computing device 10 may further include various elements. The program may include instructions which make the processor 11 to perform methods or operations according to various embodiments of the present disclosure when loaded on the memory 13. In other words, the processor 11 may perform methods or operations according to various embodiments of the present disclosure by executing the instructions. The program includes a series of computer-readable instructions that are grouped by function and is executed by the processor.

The processor 11 controls overall operation of each element of the computing device 10. The processor 11 may be configured to include at least one of a central processing unit (CPU), a microprocessor unit (MPU), a microcontroller unit (MCU), a graphics processing unit (GPU), and any form of processor well known in the technical field of the present disclosure. Further, the processor 11 may perform computation for at least one application or program to execute methods or operations according to embodiments of the present disclosure.

The memory 13 stores various kinds of data, commands, and/or information. To execute methods or operations according to various embodiments of the present disclosure, the memory 13 may load one or more programs from the storage 15. The memory 13 may be implemented as a volatile memory such as a random access memory (RAM), but the technical scope of the present disclosure is not limited thereto.

The storage 15 may non-temporarily store the program. The storage 15 may include a non-volatile memory, such as a read only memory (ROM), an erasable programmable ROM (EPROM), an electrically erasable programmable ROM (EEPROM) or a flash memory, a hard disk, a removable disk, or any form of computer-readable recording medium well known in the art to which the present disclosure pertains.

The communication interface 17 supports wired or wireless Internet communication of the computing device 10. Further, the communication interface 17 may support various communication methods as well as Internet communication. To this end, the communication interface 17 may include a communication module well known in the technical field of the present disclosure.

The bus 19 provides a communication function between elements of the computing device 200. The bus 19 may be implemented as various forms of buses, such as an address bus, a data bus, and a control bus.

The embodiments of the present invention described above are not implemented through only the apparatus and the method, but may also be implemented through a program that realizes functions corresponding to the configuration of the embodiments of the present invention or a recording medium on which the program is recorded.

While this invention has been described in connection with what is presently considered to be practical embodiments, it is to be understood that the invention is not limited to the disclosed embodiments, but, on the contrary, is intended to cover various modifications and equivalent arrangements included within the spirit and scope of the appended claims.

What is claimed is:

1. A method of reading a medical image by a computing device operated by at least one processor, the method comprising:
    obtaining an abnormality score of an input image using an abnormality prediction model;
    excluding the input image from being subsequently analyzed and classifying the input image as strong normal, when the abnormality score is less than or equal to a cut-off score based on the cut-off score which makes a specific reading sensitivity; and
    obtaining an analysis result of the input image using a classification model that distinguishes the input image into weak normal or abnormal when the abnormality score is greater than the cut-off score.

2. The method of claim 1, wherein the classification model includes an artificial intelligence model that has learned a task of distinguishing the input image into weak normal or abnormal.

3. The method of claim 1, further comprising adding the analysis result to a reading worklist,
    wherein the input image whose abnormality score is less than or equal to the cut-off score is not added to the reading worklist.

4. The method of claim 1, wherein obtaining the abnormality score comprises, when obtaining disease prediction scores for different diseases from the abnormality prediction model, aggregating the disease prediction scores to determine the abnormality score.

5. The method of claim 4, wherein obtaining the abnormality score comprises obtaining calibrated disease prediction scores, through calibration that converts a cut-off score for each disease, which makes the specific reading sensitivity, into the cut-off score, and determining a maximum value among the calibrated disease prediction scores as the abnormality score.

6. The method of claim 1, wherein excluding the input image comprises, in a case where each of disease prediction scores for different diseases is obtained as an abnormality score for each disease from the abnormality prediction model, calculating a cut-off score for each disease which makes the specific reading sensitivity, and excluding the input image when the abnormality score for each disease is less than or equal to the cut-off score for a corresponding disease, for all of the different diseases.

7. The method of claim 1, wherein the abnormality prediction model comprises:

a feature extraction model trained to output a feature of the input image; and at least one disease prediction head model trained to predict at least one disease based on features output from the feature extraction model.

8. The method of claim 1, wherein the abnormality prediction model has a sensitivity between 90% and 100%.

9. A method of reading a medical image by a computing device operated by at least one processor, the method comprising:

setting a cut-off score that makes a specific reading sensitivity for an abnormality prediction model that outputs an abnormality score of a medical image;

obtaining an abnormality score of an input image using the abnormality prediction model;

when the abnormality score of the input image is less than or equal to the cut-off score, classifying the input image as strong normal and excluding the input image from being subsequently analyzed; and obtaining an analysis result of the input image using a classification model that distinguishes between weak normal and abnormal when the abnormality score of the input image is greater than the cut-off score.

10. The method of claim 9, further comprising adding the analysis result to a reading worklist, wherein the input image classified as strong normal is not added to the reading worklist.

11. The method of claim 9, wherein obtaining the abnormality score comprises, when obtaining disease prediction scores for different diseases from the abnormality prediction model, calibrating the disease prediction scores so as to provide the specific reading sensitivity for the different diseases at the cut-off score, and determining a maximum value among the calibrated disease prediction scores as the abnormality score of the input image.

12. The method of claim 9, wherein excluding the input image comprises, in a case where each of disease prediction scores for different diseases from the abnormality prediction model is obtained as an abnormality score for each disease, calculating a cut-off score for each disease which makes the specific reading sensitivity, and excluding the input image when the abnormality score for each disease is less than or equal to the cut-off score for a corresponding disease, for all of the different diseases.

13. A method of reading a medical image by a computing device operated by at least one processor, the method comprising:

inputting an input image to an abnormality prediction model that outputs an abnormality score of a medical image, and obtaining disease prediction scores for a plurality of diseases from the abnormality prediction model, calibrating the disease prediction scores so as to provide a same reading sensitivity for the plurality of diseases at a same cut-off score, and determining a maximum value among the calibrated disease prediction scores as an abnormality score of the input image; and when the abnormality score of the input image is less than or equal to the cut-off score, classifying the input image into strong normal and excluding the input image from being subsequently analyzed, wherein the abnormality prediction model comprises:

a feature extraction model trained to output a feature of the input image; and a plurality of disease prediction head models that are trained to predict the plurality of diseases based on features output from the feature extraction model.

14. The method of claim 13, wherein the input image includes a chest x-ray image, and wherein the plurality of diseases includes at least two of consolidation, nodule, and pneumothorax.

15. The method of claim 13, wherein the reading sensitivity has a value between 90 and 100%.

16. The method of claim 13, further comprising obtaining an analysis result of the input image using a classification model that distinguishes between weak normal and abnormal when the abnormality score of the input image is greater than the cut-off score; and adding the analysis result to a reading worklist, wherein the input image classified into strong normal is not added to the reading worklist.

17. A computing device comprising:

a memory that stores an abnormality prediction model trained to output an abnormality score of an input image, and a classification model trained to distinguish the input image into weak normal and abnormal; and a processor that obtains an abnormality score of the input image using the abnormality prediction model, classifies the input image into strong normal and excludes the input image from being subsequently analyzed when the abnormality score of the input image is less than or equal to a cut-off score, and obtains an analysis result of the input image using the classification model that distinguishes the input image into weak normal or abnormal when the abnormality score of the input image is greater than the cut-off score.

18. The computing device of claim 17, wherein the abnormality prediction model comprises:

a feature extraction model trained to output a feature of the input image; and at least one disease prediction head model trained to predict at least one disease based on features output from the feature extraction model.

* * * * *